US009107920B2

(12) United States Patent
Olsen

(10) Patent No.: US 9,107,920 B2
(45) Date of Patent: Aug. 18, 2015

(54) **EXTRACT OF *TRIGONELLA FOENUM-GRAECUM***

(75) Inventor: Jens Steen Olsen, Havdrup (DK)

(73) Assignee: V-BIOTEK HOLDING APS, Copenhagen (DK)

( * ) Notice: Subject to any disclaimer, the term of this patent is extended or adjusted under 35 U.S.C. 154(b) by 837 days.

(21) Appl. No.: 12/595,715

(22) PCT Filed: Apr. 14, 2008

(86) PCT No.: PCT/DK2008/050086
§ 371 (c)(1),
(2), (4) Date: Nov. 17, 2009

(87) PCT Pub. No.: WO2008/125120
PCT Pub. Date: Oct. 23, 2008

(65) Prior Publication Data
US 2010/0129296 A1    May 27, 2010

Related U.S. Application Data

(60) Provisional application No. 60/911,653, filed on Apr. 13, 2007.

(51) Int. Cl.
*A61K 36/48* (2006.01)

(52) U.S. Cl.
CPC ...................................... *A61K 36/48* (2013.01)

(58) Field of Classification Search
CPC .................................................... A61K 36/48
USPC ........................................................ 424/776
See application file for complete search history.

(56) References Cited

U.S. PATENT DOCUMENTS

| | | | | |
|---|---|---|---|---|
| 3,620,919 | A  * | 11/1971 | Hardman | 435/267 |
| 2005/0153001 | A1 * | 7/2005 | Aburdeineh et al. | 424/757 |
| 2005/0238738 | A1 * | 10/2005 | Lee et al. | 424/757 |

OTHER PUBLICATIONS

Ziya Al-Din Abdullah Al-Jaam'e-li-Mufradaat-alAdvia-wal-Aghzia, vol. II (13th century AD), Matba Amra, Cairo, Egypt, 1874 AD, p. 25.*
Mohammad Akmal Khan Qaraabaadeen Azam wa Akmal (20th century AD), Matba Siddiqi, Delhi / Matba Mustafai, Delhi, 1909 AD, p. 167.*

Yang (Shizhen Guoyi Guoyao (2006), vol. 17, No. 8, pp. 1503-1504).*
English translation of Yang (Shizhen Guoyi Guoyao (2006), vol. 17, No. 8, pp. 1503-1504).*
Dixit (Phytotherapy Research (2005), vol. 19, pp. 977-983).*
Short Communication; Nematicidal activity of *Trigonella foenum-graecum* L; Phytotherapy Research; Feb. 8, 2000.
Spinal serotonergic system is partially involved in antinociception induced by *Trigonella foenum-graecum* (TFG) leaf extract; Parvizpur, et al.; Journal of Ethno Pharacology; May 19, 2002.
The Effect of an ethanol extract derived from fenugreek (*Trigonella foenum-graecum*) on bile acid absorption and cholesterol levels in rats; Start, et al.; Department of Biochemistry and Human Nutrition, Faculty of Agriculture, Hebrew University, Rehovot 76100, Israel; Mar. 12, 1991.
Immunomodulatory effects of fenugreek (*Trigonella foenum graecum* L.) extract in mice; Bilal Bin-Hafeez, et al.,; Department of Medical Elementology and Toxicology, Jamia Hamdard, Hamdard University, New Delhi, 110 062, India; Apr. 19, 2002.
Aqueous extract of *Trigonella foenum-graecum* L. ameliorates additive urotoxicity of buthionine sulfoximine and cyclophosphamide in mice; K. Bhatia, et al.; Department of Medical Elementology and Toxicology; Jamia Handard (Handard University), New Deljhi 110 062, India; Dec. 8, 2005.
Phenolics, their antioxidant and antimicrobial activity in dark germinated fenugreek sprouts in response to peptide and phytochemical elicitors; Reena Randhir, et al.; Department of Food Science, Chenoweth Laboratory, University of Massachusetts, Amherst, MA 01003, USA; Apr. 23, 2004.
Bactericidal and anti-adhesive properties of culinary and medicinal plants against *Helicobacter pylori*; Rachel O'Mahony, et al.; World of Gastrinterology; ISSn 1007-9327; 2005.
Effects of Material and Extracts of *Trigonella foenum-graecum* L. Against the Stored Product Pests *Tribolium castaneum* (Herbst) (Coleoptera: Tenebrionidae) and *Acanthoscelides obtectus* (Say) (Coleoptera: Bruchidae); Jerome Pemonge, et al.; Feb. 7, 1997.

* cited by examiner

*Primary Examiner* — Susan Hoffman
(74) *Attorney, Agent, or Firm* — Sughrue Mion, PLLC

(57) ABSTRACT

Disclosed herein is an extract obtainable from *Trigonella foenum-graecum*. In particular, the extract is obtainable by a process comprising the steps of preparing a mixture of a plant material obtained from *Trigonella foenum-graecum* and liquid, incubating said mixture for at least 3 hours, heating of said mixture, and recovering a liquid extract from mixture. The extract is useful in the manufacture of various types of compositions, such as pharmaceutical compositions, disinfectant or preservation agents. The pharmaceutical may be used for the treatment or prevention of an inflammatory disease or an infectious condition.

7 Claims, 1 Drawing Sheet

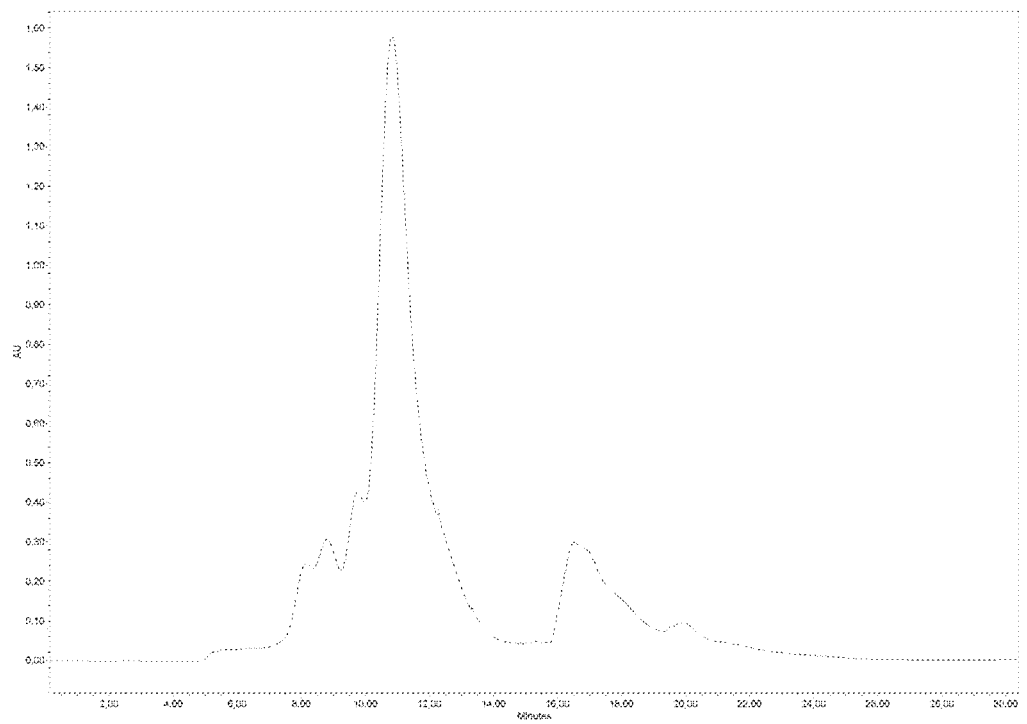

**EXTRACT OF *TRIGONELLA FOENUM-GRAECUM***

CROSS REFERENCE TO RELATED APPLICATION

This application is a National Stage of International Application No. PCT/DK2008/050086 filed Apr. 14, 2008, claiming priority based on U.S. Provisional Patent Application No. 60/911,653, filed Apr. 13, 2007, the contents of all of which are incorporated herein by reference in their entirety.

All patent and non-patent references cited in the application are hereby incorporated by reference in their entirety.

FIELD OF INVENTION

The present invention relates to an extract of *Trigonella foenum-graecum* and compositions comprising this extract. Furthermore the invention relates to uses of the extract and methods making use of the extract. Notably, the invention relates to pharmaceutical compositions comprising said extract and use thereof in the treatment of inflammatory and infectious conditions. Another aspect of the present invention relates to the use of the extract of *Trigonella foenum-graecum* for or in the preparation of disinfactants or cleansing products.

BACKGROUND OF INVENTION

Fenugreek (*Trigonella Foenum-Graecum*)

Fenugreek (*Trigonella foenum-graecum*) commonly known as Bird's foot, Greek hayseed, trigonella, bockshornsame, Methi, and hu lu ba, is a herb known in the art of integrative medicine.

Fenugreek is used both as an herb (the leaves) and as the seeds. Fenugreek and products thereof are traditionally used as a demulcent, laxative, lactation stimulant. Fenugreek is a common constituent in the ayurvedic medicine. Fenugreek and products thereof have been proposed for treatment conditions as diverse as alopecia, arthritis, cancer, diabetes, gastro-intestinal disorders, high cholesterol, induce childbirth, infections, inflammation, stimulation of lactation, lymphadenitis, muscle pain, promote urination, skin ulcers, wound healing. Extracts of fenugreek show antimicrobial and nematocidal activity in vitro (reference: Zia et al. (2001) *Phytotherapy Research* 15:538). The mechanism of action is not well characterized. Most traditional uses of fenugreek are likely attributable to its high fibre content.

The FDA lists fenugreek as "generally regarded as safe", although side effects such as bleeding, bruising, flatulence, diarrhea, gastrointestinal disturbances, and hypoglycemia have been reported.

According to references cited at Memorial Sloan-Kettering Cancer Center's site regarding use of herbs in integrative medicine, the following substances are identified in fenugreek: Alkaloids: Trigonelline (yields nicotinic acid with roasting), gentianine, carpaine, choline; Proteins and amino acids: 4-Hydroxyisoleucine, histidine, lysine, arginine; Flavonoids: Apigenin, luteolin, orientin, vitexin, quercetin; Saponins: Graecunins, fenugrin B, fenugreekine, trigofoenosides A-G; Steroidal sapinogens: Yamogenin, diosgenin, smilagenin, sarsasapogenin, tigogenin, neotigogenin, gitogenin, neogitogenin, yuccagenin; Fiber: Gum, neutral detergent fiber; Other: Coumarin, lipids, vitamins, minerals.

One of the constituents of fenugreek, saponin is a mild detergent and used in applications such gently clean ancient manuscripts and textiles. In research the membrane permeabilizing properties are used in intracellular histochemistry staining applications to allow antibody access to intracellular proteins due to the membrane.

SUMMARY OF INVENTION

One aspect of the present invention relates an extract obtainable by a process comprising the steps of preparing a mixture of a plant material obtained from *Trigonella foenum-graecum* and liquid, incubating said mixture for at least 3 hours, heating of said mixture, and recovering a liquid extract from mixture.

The extract may be included in various types of compositions, such as pharmaceutical compositions, disinfectant or preservation agents.

Another aspect of the present invention relates to the use of said extract, such as in the preparation of a medicament for the treatment or prevention of an inflammatory disease or an infectious condition.

BRIEF DESCRIPTION OF THE DRAWINGS

FIG. 1 is a chromatogram relating to an Example provided in the specification.

DETAILED DESCRIPTION OF THE INVENTION

The present invention concerns an extract from fenugreek obtainable by a certain method and compositions comprising said extract for treatment of ia. infections. Infections include bacterial infection, other microbial infection and viral infection. Preferably the infections are cutaneous infection, mucous membranes, infections in the gastro-intestinal tract, and infections in the throat and mouth cavity. Subjects for treatment of said extract and compositions thereof are human beings and mammals, preferably human beings and domestic animals. The present invention also related to the treatment of inflammatory conditions, which may be caused by or associated with an infection.

Method of Preparing an Extract of *Trigonella Foenum-Graecum*

One aspect of the invention relates to the preparation of an extract of plant material of a least one plant of the genus *Trigonella*. In the preferred embodiment said plant material is obtained from *Trigonella foenum-graecum*.

The method of preparing said extract according to the invention comprises:
a. preparing a mixture of plant material and liquid,
b. incubating said mixture for at least 3 hours,
c. heating of said mixture,
d. recovering a liquid extract from mixture eg. by separating remaining plant material from the mixture.

The plant material may be whole plant, leaves, seeds or roots of said plant, or combinations of said plant materials. The plant material may be fresh, frozen, dried or combinations thereof. The preferred embodiment the plant material is seeds of *Trigonella foenum-graecum*, most preferably dried seeds of said plant.

In order to facilitate the extraction of the active ingredients of the plant material, said plant material is soaked in a liquid preferably water. The mixture of liquid and plant material is incubated for at least 3 hours, more preferably at least 6 hours, preferably at least 12 hours, such as at least 24 hours. The incubation is usually performed at temperatures between 0 and 45° C., suitably at temperatures between 10 and 40° C.

Subsequently, the mixture comprising the plant material soaked in a liquid is heated, preferably to a temperature above the coagulation of proteins. In a certain aspect the mixture is boiled.

The mixture according to the invention comprises plant material and a liquid. The ratio by weight of said plant material and said liquid in said mixture 1 to 1, or preferably less plant material by weight such as 1 to 2, or less plant material by weight such as 1 to 3, or less plant material by weight such as 1 to 4, or less plant material by weight such as 1 to 5, or less plant material by weight such as 1 to 6, or less plant material by weight such as 1 to 7, or less plant material by weight such as 1 to 8, or less plant material by weight such as 1 to 9, or less plant material by weight such as 1 to 10. In a preferred embodiment the ratio by weight of said plant material and said liquid is 1 to 6.

During the heating of the mixture additional liquid may be added at least once in order to compensate for evaporated liquid and liquid taken up by the plant material. The liquid is heated for at least 5 minutes, such as 10 to 45 minutes, more preferably 20 to 30 minutes, such as 20 minutes. The heating may be terminated when the embryo is released from the seeds, which is associated with increased viscosity of the mixture.

In one embodiment, the mixture is frozen (preferably at −18° C.) prior to or after the heating step for at least 3 hours, preferably more than 6 hours, such as 12 hours, or more than 12 hours. Subsequently, the mixture may be subjected to a second round of heating before recovery of the extract, eg. by removing the remaining plant material. The freezing step is anticipated further to enhance the release of the active ingredients from the plant material.

The volume of a final concentrated extract originating from ½ kg of plant material such as seeds is approximately 2 liters.

For long term conservation the extract may be refrigerated. Depending on the application the extract may be diluted in water or used as it is. The extract may be further concentrated by removal of solvent. The solvent may be removed by any appropriate means, such as membrane filtration, evaporation, precipitation, extraction, azeotrope distillation, lyophilisation, spray drying and combinations thereof.

Without being bound by the theory it is believed that the method described herein results in the efficient release of one or more active ingredients from the plant material. As described in the background section, plants and plant materials such as plant material from *Trigonella foenum-graecum* comprise active ingredients displaying diverse effects.

The extract of the invention may be purified to isolate the active ingredient(s) by any appropriate method. Thus, the extract may be fractioned using gel filtration, HPCL, extraction, precipitation, etc. In a presently useful method the extract is fractioned using HPLC. In a specific method the active ingredient(s) is included in an extract fraction obtainable by performing reverse phase chromatography on a size B Lichroprep RP-18 (40-63 μm) (Merck) of the basis extract using the following gradient: 0-1 min H$_2$O/AcN 98:2, then using a steady gradient from 1-40 min going to 100% and collecting the fraction at the time interval between 5 and 10 min.

The extract obtained by the method according to the invention is particular useful for the indications described herein, which are believed to reflect the profile of the active ingredient(s) released from the plant material to the extract in term of quality and quantity.

For comparison purposes an extract was prepared without the incubation step. The HPLC analysis of the extract according to the invention and the extract prepared for comparison show a considerable difference in composition. The analysis is reported in example 13.

Conditions within the Scope of Treatment
Infections

The term "infection" refers to the detrimental colonization of a host organism by a foreign infectious species. The host's response to infection is inflammation. Infectious species include bacteria, parasites, fungi and viruses.

One aspect according to the invention concerns the use of a composition comprising extract of plant material such as extract of fenugreek as described herein for the treatment of infections conditions.

Bacterial Infection

By "bacterial infection" in the present context is meant the invasion of normally sterile host tissue by bacteria. Bacterial infection of the invention may be due to invasion of either Gram negative or Gram positive bacteria, or a combination thereof or other infectious agents including fungi and virus.

A preferred embodiment according to the invention concerns the use of a composition comprising extract of plant material such as extract of fenugreek as described herein for the treatment of bacterial infections. In another embodiment according to the invention the infection is a combination of bacterial infection and infection by another species such as fungi and virus.

Impetigo

The term "impetigo" refers to several different infectious skin diseases. Impetigo contagiosa is a superficial, intraepidermal, unilocular, vesiculopustular infection. Impetigo contagiosa is the most common skin infection in children. Bullous impetigo is a toxin-mediated erythroderma in which the epidermal layer of the skin sloughs resulting in large areas of skin loss. Common impetigo is the term applied when the infection occurs in preexisting wounds. Impetigo also can present as folliculitis, which is considered to be impetigo of the hair follicles caused by *Staphylococcus aureus*. Eethyma is a deeper, ulcerated impetigo infection, often occurring with lymphadenitis. Two main types of bacteria cause impetigo: streptococcal and staphylococcal organisms. Both are commonly found in the environment and on the surface of most people's skin.

An embodiment according to the present invention concerns the use of a composition comprising extract of fenugreek as described herein for the treatment of impetigo.

In one embodiment according to the invention the conditions is caused by Streptococcal and Staphylococcal infections such as *Staphylococcus aureus*

Periodontal Diseases

Periodontitis (periodontosis, paradentosis, pyorrhea) is a dental disorder that results from progression of gingivitis, involving inflammation and infection of the ligaments and bones that support the teeth.

Left untreated for years it may results in loss of bone supporting the teeth and final loss of teeth. The conditions may involve one or more teeth.

Gingivitis is associated with little or no discomfort apart from redden, swollen and easily bleeding gums. Gingivitis is often caused by inadequate oral hygiene leaving the bacteria in plaque on the teeth causing the gums to become inflamed. Gingivitis is reversible with professional treatment and good oral home care. If gingivitis is left untreated plaque can spread and grow below the gum line and the condition may advance to periodontitis. Toxin released by bacteria in the plaque initiate an inflammatory response in the gums, which may become chronic and destroy the bone supporting the teeth. Gums separate from the teeth, forming pockets (spaces between the teeth and gums) that become infected. As the disease progresses, the pockets deepen and more gum tissue and bone are destroyed. Often, this destructive process has very mild symptoms. Eventually, teeth can become loose and may have to be removed.

Chronic periodontitis is recognized as the most frequently occurring form of periodontitis. Chronic periodontitis results in inflammation within the supporting tissues of the teeth, progressive attachment and bone loss and is characterized by pocket formation and/or recession of the gums (gingiva). It is prevalent in adults and a major cause of loss of teeth in adults, but the disease can occur at any age. Progression of attachment loss usually occurs slowly, but periods of rapid progression can occur.

Aggressive periodontitis is a condition that affects patient who are otherwise clinically healthy. Common features include rapid attachment loss and bone destruction and familial aggregation. Periodontititis, often with onset at a young age, associated with one of several systemic diseases, such as diabetes or osteoporosis (Periodontitis as a manifestation of systemic diseases). Necrotizing periodontal diseases is another form of infection characterized by necrosis of gingival tissues, periodontal ligament and alveolar bone. This condition is most often associated with systemic conditions including, but not limited to, HIV infection, malnutrition and immunosuppression.

Apart from is bacterial plaque other factors affecting the health of the gums include: Smoking, genetics, pregnancy, puberty, stress, medication, clenching/grinding of teeth, poor nutrition, diabetes and other systemic diseases.

Gingtivitis usually disappears with good self-care. In contrast, periodontitis requires repeat professional care. A person using good oral hygiene can clean only 2 to 3 millimeters (1/12 inch) below the gum line. A dentist can clean pockets up to 4 to 6 millimeters deep (1/5 inch) using scaling and root planing, which thoroughly remove tartar and the diseased root surface. For pockets of 5 millimeters (1/4 inch) or more, surgery is often required. A dentist or periodontist may access the tooth below the gum line surgically (periodontal flap surgery) to thoroughly clean the teeth and correct bone defects caused by the infection. A dentist or periodontist may also remove part of the infected and separated gum (a gingivectomy) so that the rest of the gum can reattach tightly to the teeth and the person can then remove the plaque at home. A dentist may prescribe antibiotics (such as tetracyclines or metronidazole), especially if an abscess has developed. A dentist may also insert antibiotic-impregnated materials (filaments or gels) into deep gum pockets, so that high concentrations of the drug can reach the diseased area. Periodontal abscesses cause a burst of bone destruction, but immediate treatment with surgery and antibiotics may allow much of the damaged bone to grow back. If the mouth is sore after surgery, a chlorhexidine mouth rinse used for 1 minute twice a day may be temporarily substituted for brushing and flossing.

If a patient has 5 millimeters (1/4 inch) or deeper pockets around most of their teeth, then they would then risk loss of all of their teeth over the years. If this not identified and the patient remains unaware of the progressive periodontal disease then, years later, they may be surprised that most of the teeth have suddenly seemed to become loose and that most or all of them may need to be extracted.

Pharmaceutical systemic treatment of gingivitis, periodontitis (aggressive and chronic), periodontitis as a manifestation of systemic diseases, and necrotizing periodontal diseases using tetracyclines is associated with a number of disadvantages the rapid emergence of tetracycline resistant bacterial strains and the occurrence of overgrowth of unsusceptible pathogens, such as *Candida*, during treatment. Short term treatment of periodontal infection with tetracyclines is often ineffective. Penicillins, which in general are highly effective antimicrobial compositions against anaerobic bacteria, have been shown to be ineffective against bacterial species important in peridental infections (e.g. *P. gingivalis*).

The limitations and disadvantages described above for the currently used surgical and non-surgical therapies reveal the unmet need for effective treatment of these dental conditions.

One embodiment according to the invention concerns the use of a composition comprising extract of plant material such as extract of fenugreek as described herein for the treatment of infections in the mouth cavity.

One highly preferred embodiment according to the present invention relates to the use of a composition comprising extract of plant material such as extract of fenugreek as described herein for the treatment of a periodontal disease such as gingivitis, periodontitis (aggressive and chronic), periodontitis as a manifestation of systemic diseases, and necrotizing periodontal diseases.

Halitosis (or bad breath) is a very common temporary condition such as "morning breath". Chronic halitosis, which is a more serious and persistent condition, is usually caused by persistent overpopulation of certain types of oral bacteria. Chronic halitosis is often associated with the periodontal diseases described herein.

In one embodiment according to the invention a composition comprising extract of plant material such as extract of fenugreek as described herein is used for the treatment of halitosis. In a preferred embodiment said halitosis is chronic halitosis.

Pharyngitis

Pharyngitis also known as sore throat is pain in the posterior pharynx, with or without swallowing. Most causes are infectious either viral or bacterial (such as streptococcal pharyngitis).

In one embodiment according to the invention a composition comprising extract of plant material such as extract of fenugreek as described herein is used for the treatment of pharyngitis. In another embodiment according to the invention said pharyngitis is streptococcal pharyngitis.

Viral Infection

Viral infection refers to an infection caused by a virus. Unlike bacteria viral replication is dependent on a host cell employing the host systems such as the transcription factor and translational machinery. The most common human diseases caused by viruses include common cold, the flu, cold sores, and warts.

In one embodiment according to the present invention a composition comprising extract of plant material such as extract of fenugreek as described herein is used in the treatment of viral infections such as common cold, the flu, cold sores, and warts.

Cold Sores

Cold sores (oral herpes, Herpes labialis) are caused by herpes simplex virus 1 (HSV-1) infection, which manifests itself as painful, watery blisters in the skin or mucous membranes located on the mouth or lips.

Available treatments of cold sores include the use antiviral medications such as Aciclovir and Valaciclovir, which reduces the duration of symptoms and accelerates healing. There is no cure for the conditions.

In a preferred embodiment according to the present invention a composition comprising extract of plant material such as extract of fenugreek as described herein is be used in the treatment of cold sores.

Common Cold

Common cold (actute viral nasopharyngitis) is a mild viral infectious disease of the upper respiratory system. Common cold is the most common of all human diseases and the condition typically last for a few days with residual symptoms of coughing lasting for another few weeks. The viral transmission between individual is efficient and children, family members and caretakers are at high risk. The incidence of common cold is high, several infections per adult per year and even more for children. Viruses associated with common cold include rhinoviruses, coronaviruses, and also certain echoviruses, paramyxoviruses, and coxsackieviruses. Common cold itself is not life threatening however it weakens the immune system and further complication may arise such as pneumonia. There is to date no proven cure for common cold.

In one embodiment according to the present invention a composition comprising extract of plant material such as extract of fenugreek as described herein is be used in the treatment of common cold.

Warts

Warts are common benign epidermal lesions associated with human papillomavirus infection (HPV) infection. Warts referrers to a range of conditions, which differs in type of papillomavirus causing the conditions, the morphology, appearance on the body such as on the fingers, the foot, the face such as the lips or near the eyelids, or genital areas. Example of warts include common wart (verruca vulgaris) caused by HPV 1, 2, 4, 27, and 29, flat wart (verruca plana) caused by HPV 3, 10, 28, and 49, filiform or digitate wart, Palmar and plantar wart (verruca, verruca pedis) caused by HPV 1, mosaic wart, and genital wart (venereal wart, condyloma acuminatum, verruca acuminata).

Apart from being painful warts may also be a cosmetic problem there is no effective treatment of warts, which frequently reoccur a few months or years after the available treatment has been terminated.

In a preferred embodiment according to the invention the extract or a composition comprising said extract is used for the treatment of warts such as warts located on the fingers, the foot, the face such as the lips or near the eyelids, or genital areas.

Infection in the Eyes and the Area Around the Eyes

An embodiment according to the invention relates to the use of extract or a composition comprising said extract for the treatments of infections in the eyes and/or the adnexa of the eyes such as the eyelids. The condition may involve inflammation, bacterial infection, viral infection or combinations thereof.

Inflammation

Inflammation is a defence reaction caused by tissue damage due to a mechanical injury or bacterial, virus or other organism infection. The inflammatory response involves three major stages: first, dilation of capillaries to increase blood flow; second, microvascular structural changes and escape of plasma proteins from the bloodstream; and third, leukocyte transmigration through endothelium and accumulation at the site of injury and infection. The inflammatory response begins with a release of inflammatory mediators. Inflammatory mediators are soluble, diffusible molecules that act locally at the site of tissue damage and infection, and at more distant sites, influencing consequent events of the inflammatory response. Inflammatory mediators can be exogenous, e.g. bacterial products or toxins, or endogenous, which are produced within the immune system itself, as well as injured tissue cells, lymphocytes, mast cells and blood proteins. Inflammatory conditions are associated with a variety of tissues. Examples of inflammatory conditions asthma, dermatitis such as diaper dermatitis, acne, inflammatory conditions in the gastro-intestinal tract such as Crohn's disease, inflammatory bowel disease (such as Ulcerative colitis).

In one embodiment according to the present invention a composition comprising extract of plant material such as extract of fenugreek as described herein is used in the treatment of a condition comprising inflammation such as asthma, dermatitis such as diaper dermatitis, acne, inflammatory conditions in the gastro-intestinal tract such as Crohn's disease, inflammatory bowel disease (such as Ulcerative colitis).

In one preferred embodiment according to the invention the extract or a composition comprising said extract is used for the treatment of acne (acne vulgaris), which a common inflammatory condition of the skin often associated with bacterial infection.

In another preferred embodiment according to the invention the extract or a composition comprising said extract is used for the treatment of acne (acne vulgaris) comprising bacterial infection.

In another preferred embodiment according to the invention the extract or a composition comprising said extract is used for the treatment of dermatitis such as diaper dermatitis (diaper rash).

Wounds

The term "wound" refers to lesion of skin or mucosa (such as oral mucosa, gastric- and intestinal mucosa). The wound may be a result of and infection, injury, or surgery. Wound according to the invention also include chronic wounds and ulcers.

One preferred embodiment according to the invention relates to the use of a composition comprising extract of plant material such as extract of fenugreek as described herein is used for the treatment of or preventing infection of a wound such as a surgical wound, a incised wounds, a penetration wound, a puncture wound, an abrasion, a chronic wound, or an ulcer.

Wounds may also results from bites. Human and mammal (mostly dog and cat, but also squirrel, gerbil, rabbit, guinea pig, and monkey) bites are common and occasionally cause significant morbidity and disability. The hands, extremities, and face are most frequently affected, although human bites can occasionally involve breasts and genitals. In addition to tissue trauma, infection from the biting organism's oral flora is a major concern.

In one embodiment according to the invention a composition comprising extract of plant material such as extract of fenugreek as described herein is used for the treatment of bites caused a human or a mammal, preferably a dog.

Compositions Comprising Extract of *Trigonella Foenum-Graecum*

In one embodiment according to the present invention extract of plant material preferably extract of *Trigonella foenum-graecum* is used for the preparation of a pharmaceutical composition.

Concentrates of the extract of the invention or fractions of the extract is also with in the scope of the invention. In particular, concentrates in which essentially all solvent has been removed and the extract is present as a dry powder may be used for the preparation of a medicament. As some fractions of the extract have shown higher effects than others, it is preferred in a certain aspect of the invention to use the fractions containing the active components for producing the pharmaceutical composition.

The pharmaceutical composition comprising an extract of *Trigonella foenum-graecum* may be formulated in a number of different manners, depending on the purpose of the particular medicament and the type of administration. It is well within the scope of a person skilled in the arts to formulate compositions that are in accordance with the preferred type of administration.

The medicament comprising the extract according to the invention may be prepared by any conventional technique, e.g. as described in Remington: The Science and Practice of Pharmacy 1995, edited by E. W. Martin, Mack Publishing Company, 19th edition, Easton, Pa.

The medicament may comprise pharmaceutical acceptable additives such as any conventionally used pharmaceutical acceptable additive, which should be selected according to the specific formulation, intended administration route etc. For example the pharmaceutical acceptable additives may be any of the additives mentioned in Nema et al, 1997. Furthermore, the pharmaceutical acceptable additive may be any accepted additive from FDA's "inactive ingredients list", which for example is available on the internet address http://www.fda.gov/cder/drug/iig/default.htm Topical Administrations Forms One preferred embodiment of the present invention is to provide a pharmaceutical composition formulated for topical application on a local, superficial and restricted area such as the a wound, a cold sore, a wart, acne, diaper rash.

In said above-mentioned embodiment, the medicament may be formulated as an ointment, a lotion, a crème, a bath admixture, a gel, a paste, a milk, a suspension, an aerosol, a spray, a film, a foam, a serum, a swab, a pledget, a pad, a patch, a powder, a paste, a liniment, viscous emulsion, porridge, or another formulation which is appropriate for topical administration.

Such compositions for topical administration may further include physiologically acceptable components such as carriers, surfactants, preservatives, stabilizing agents, buffers, excipients and emulsifiers suited for this type of administration. Suitable components for topical delivery systems are preferably chosen from components that do not cause excessive or unavoidable irritation or pain to the recipient. Carriers include diluents and provide the medium in which the pharmaceutical constituents are dissolved, dispersed or distributed.

The medicament according to the invention may comprise, but are not restricted, a carrier such as an aqueous liquid base, nonaqueous liquid base, water soluble gel, a mineral oil base, emulsion, ointment, crème, gel or lotion, suspension of solid particles in a liquid.

The topical availability of drugs depends on two contrasting factors: their ability to dissolve in the carrier (gel, creme—hydrophilic), and their ability to permeate the skin barrier (ie, the stratum corneum—hydrophobic), thus requiring a unique hydrophobic-hydrophilic balance. Formulations require addition of excipients, such as permeation enhancers and solubilizers to facilitate either or both of the transport processes (dissolution into vehicle and diffusion across skin). Additives, such as alcohols, fatty alcohols, fatty acids, mono- di- or tri-glycerides, glycerol monoethers, cyclodextrin and derivatives, polymers, bioadhesives, terpenes, chelating agents and surfactants have been disclosed to increase transdermal delivery of drugs. It is within the present invention to make use of such excipients.

Any method, not limited to the above-mentioned, for increasing transdermal delivery is within the scope of the present invention. The medicament according to the present invention may therefore comprise surfactants such as ionic and/or non-ionic surfactants. Suitable non-ionic surfactants include for example: fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); alkyl polyglycosides, N-alkyl-, N-alkoxypolyhydroxy fatty acid amide, in particular N-methyl-fatty acid glucamide, sucrose esters; sorbitol esters, esters of sorbitol polyglycol ethers and lecithin. Ionic surfactants include for example sodium lauryl sulfate, sodium laurate, polyoxyethylene-20-cetylether, Laureth-9, sodium dodecylsulfate (SDS) and dioctyl sodium sulfosuccinate.

Alcohols include, but are not limited to, ethanol, 2-propanol and polyols such as polyethylene glycol (PEG), propylene glycol, glycerol, propanediol.

Methods for enhancing drug delivery through topical administration may be applied with the present invention, and include any means of increasing absorption, minimizing metabolism, and/or prolonging the half-life of the active ingredient of the medicament such as the extract of *Trigonella foenum-graecum*. Such means include the use of transporters of the type liposomes, ISCOMs, nano-particles, microspheres, hydrogels, organogels, polymers or other microencapsulation techniques.

Medicament for topical delivery according to the present invention comprising may comprise 5 to 100 wt % of the extract of *Trigonella foenum-graecum*, preferably 50 to 100 wt % by weight of said extract.

Oral Administrations Forms

Another preferred embodiment of the present invention is to provide a medicament formulated for oral administration such as a mouth wash.

In one preferred embodiment the medicament is formulated as a mouth wash such as by dilating the extract according to the invention in a liquid.

The liquid may be any useful liquid, however it is frequently preferred that the liquid is an aqueous liquid. It is furthermore preferred that the liquid is sterile. Sterility may be conferred by any conventional method, for example filtration, irradiation or heating.

It is within the scope of the present invention to supply medicament, and uses thereof, comprising extract of plant material preferably extract of *Trigonella foenum-graecum* for the treatment of clinical conditions described above involving an infection or an increased risk of acquiring an infection. For example, but not limited to, clinical conditions involving infection, or is at risk of being infection, by a microbial species. In one embodiment of the extract of *Trigonella foenum-graecum* is co-administered with at least one second active ingredient. Preferably extract of *Trigonella foenum-graecum* and said least one second active ingredient are present in the same medicament, or they may be supplied in a kit of parts. Preferably, said second active ingredient is an antimicrobial substance, for example an antiseptic, antibiotic, antifungal, antiparasitic or antiviral agent.

In an embodiment according to the present invention, the extract of plant material preferably extract of *Trigonella foenum-graecum* is constituent in a tooth-paste.

Administration of Medicament Comprising Extract of *Trigonella Foenum-Graecum*

The medicament for oral administration comprising extract of plant material preferably extract of *Trigonella foenum-graecum* may be diluted in the liquid such as water. Said medicament may comprise 5 to 100 vol/vol % of the extract and liquid.

According to the present invention "a pharmaceutical effective dosage" of the composition (such as the extract according to the invention) refers to the amount necessary to induce the desired biological effect on the subject in need of treatment.

The medicament according to the present invention may be administrated once or more than once a day, for example they may be administered in the range of 2 to 10 times a day, such as 2 to 7 times, for example 2 to 5 times, such as 2 to 4 times, such as 2 to 3 times a day.

The medicament according to the present invention may be administrated to the subject for a period of treatment of one or more than one week such as two weeks, three weeks, four weeks, five weeks, six weeks, seven weeks, eight weeks or more than eight weeks. The treatment may be repeated on subjects, who relapse.

Antiseptic/Disinfectant Comprising Extract of *Trigonella foenum-Graecum*

One aspect of the present invention relates to the use of extract or a composition comprising said extract as an antiseptic or disinfectant.

Accordingly, one embodiment according to the invention the extract of *Trigonella foenum-graecum* is formulated as an antiseptic/disinfectant for application to living tissue/skin such as a surgical wound to minimise the risk of infection.

In an embodiment extract of plant material preferably extract of *Trigonella foenum-graecum* is comprised in a soap product.

In further preferred embodiment extract of plant material preferably extract of *Trigonella foenum-graecum* according to the invention is used for the preparation of an antiseptic or disinfectant product. According to the invention said products is used for the disinfection of to non-living objects such as kitchen utensils, refrigerators, freezers, kitchen installations, floors, installations in stables or slaughterhouses.

In another preferred embodiment the extract of plant material preferably extract of *Trigonella foenum-graecum* or a composition comprising said extract is used for the cleaning of urine stains on concrete elements or concrete floors.

In an embodiment the extract of plant material preferably extract of *Trigonella foenum-graecum* or compositions comprising said extract is used as a disinfectant for drinking water.

In yet another embodiment extract of plant material preferably extract of *Trigonella foenum-graecum* or compositions comprising said extract is used for the disinfection of water tanks infected with *Legionella*. In one embodiment the water is a swimming pool.

Preservation of Food Products

The extract according to the invention may also be used as preservation for food product such as meat such as minced meat and poultry. In one embodiment the extract is mixed with minced meat before storage.

EXAMPLES

Example 1

Preparation of Extract of Seeds 500 g seeds of *Trigonella foenum-graecum* were soaked in 2 l water for approximately 24 hours. Following the presoaking the seeds were cooked for 30 minutes and remains of the seeds were removed from the mixture. The extract was chilled.

Example 2

Treatment of Warts and Lip Herpes

The extract according example 1 was used in the treatment of warts and lip herpes (Herpes labialis). The extract was applied to the area of the condition on two female patients (age 18 and 44). The conditions disappeared in few hours. The extract was tested on a male (age 44) and a female (age 48) suffering from warts localised on the foot. The warts were wounded using a needle and the extract was administrated topically to the area of the condition. In both cases the patient felt relieved from the discomfort associated only a few hours after the administration.

Example 3

Treatment of Chronic Periodontitis

Female 70 years. Chronic periodontitis and associated haliosis and bleeding gums were diagnosed at the age of 65. Apart from dental cleansing the patient was not subjected to any dental treatment. The patient was treated with the extracts according to the present invention administrated as mouth wash. After two days of treatment haliosis disappeared and after two month of treatment the inflammation of the gums and bleeding of the gums disappeared.

Example 4

Treatment of Periodontitis

Male 54 years. Periodontitis associated with haliosis was diagnosed by a dentist. The patient was treated with the extract according to the invention administrated as a mouth wash. After a few days of treatment haliosis disappeared. The disappearance of priodontitis and the healing of the gums were confirmed by a dentist a few month later. No further treatment was required.

Example 5

Wound on Leg

Male 54 years. An infected wound on the back of the leg due to a splinter of pressure-creosoted wood was treated with the extract according to the invention by topical administration on the infected area. The infection disappeared in one day.

Example 6

Wound from Dog Bite

A 44 year old male was treated for a wound resulting from a dog bite. After the bite the wound was healing but inflammation appeared after a few days. The infected matter was removed from the wound and the extract according to the invention was administrated to the wound. The pain associated with the infection of the wound immediately disappeared and the wound healing properly in a few days.

Example 7

Wounds on Animals

Infected wounds on a cat and a dog were treated with the extract according to the invention. The dog was treated two times a day for two days by topical administration on the infected area (diameter 200 mm). The wound healed properly. The cat was suffering from a severely infected wound (diameter approximately 300 mm). The wound was treated by topical administration twice a day for 3 days. The wound healed completely in two to three days.

Example 8

Treatment of Minor Wounds and Itching

A 44 year old male frequently suffering from minor wounds and itching in the area of the anus were treated with the extract according to the invention. Topical administration of the extract to the area of the conditions reveal the patient from the itching in a few minutes and the wounds healed in approximately 12 hours. No further treatment of the wounds was needed. Topical administration of a cordison liniment was less efficient.

Example 9

Treatment of Pharyngitis

Female, age 18, suffering from pharyngitis. The treatment of the conditions was washes of the mouth cavity and throat using the extract according to the invention. She reported immediate relieve of the discomfort associated with the condition.

Example 10

Pig Sore

A pig having a sore of an approximate area of 100 cm$^2$ was sprayed with a 1:1 mixture of water and the extract according to example 1. 24 hours after the treatment a film had formed on the sore. Exudation and infection was absent. After repeated treatment once a day for 4 days the sore was healed.

Example 10

Removal of Malodour

The extract produced in according with example 1 was used with success for the removal of malodour. Shoes of neoprene and inner soles of shoes were soaked in a dilution (water diluted) of the extract according to the invention and dried. Concentrated extract was applied to the shoes and soles. After the treatment there was no sign of malodour.

Urine stains (dog urine) on concrete were washed with chlorine and a universal house-hold cleansing agent with no successful removal of the malodour. Washing the stains with a dilution of the extract completely removed the malodour. The extract was also successfully used as antiperspirant, effective for more than 24 hours.

Example 11

Preservation of Minced Meat

A few drops of the extract according to the invention were added to 50 grams of minced meat. The treated meat and a corresponding sample of untreated minced meat were left for refrigeration. A severe malodour was observed from the untreated meat sample after two days of refrigeration. The treated meat appeared fresh with no malodour for five days. On day six malodour was observed from the treated sample.

Example 12

Clinical Protocol for Periodontitis

Enrolment in the Study:
20 subjects (volunteers) that meet the proposed diagnostic criteria of periodontitis are enrolled in the study.
Study:
The study is performed in a double-blinded, placebo-controlled fashion. Subjects are divided into two groups (n=10 in each), groups A and B. The subjects are instructed in self-treatment comprising 2 minutes of mouth wash twice a day using the extract according to the invention. The treatment duration is 3 months. The subjects keep diaries where they note the timing, type and severity of experienced symptoms throughout the treatment phase.
Dosing:
Group A receives the extract according to the invention. Group B receives placebo.
Evaluation of Study:
The subjects' diaries are reviewed and subjected to statistical analysis by the investigators and the severity of symptoms is determined in relation to the conditions at the entry of the study.

Example 13

Comparative Extract 500 g seeds of *Trigonella foenum-graecum* were cooked in 2 l water for approximately 30 minutes and remains of the seeds were removed from the mixture. The extract was chilled.

The extracts of example 1 and the extract of example 13 were subjected to an HPLC analysis with UV detection and light scattering.

Samples of the extract were diluted 5 times with water and filtered through a 0.45 μm nylon filter. The analyses were conducted on a Synergi Polar-RP 80A (250×4.6 mm, 4 μm, nr. 16) using 10.6 mM formic acid/methanol as eluent (98% formic acid in 15 min, gradient to 65% after 30 min, gradient to 0% after 60 min) and detected by light scattering.

Table 1 below discloses selected tops of the chromatogram:

TABLE 1

| Top nr. | RT (min) | Reference (Ex. 13) | Invention (Ex. 1) |
|---|---|---|---|
| 1 | 1.8 | 0.188 | 12.358 |
| 2 | 2.5 | 6.778 | 12.973 |
| 3 | 2.8 | 137.36 | 165.609 |
| 4 | 3.2 | 144.218 | 241.491 |
| 5 | 3.5 | 30.959 | 51.101 |
| 6 | 3.9 | 33.887 | 47.785 |
| 7 | 4.4 | 2.102 | 2.741 |
| 8 | 38.1 | 0.45 | 1.672 |
| 9 | 38.6 | 3.509 | 3.828 |
| 10 | 39.2 | 3.904 | 6.371 |
| 11 | 41.1 | 7.358 | 8.189 |
| 12 | 41.4 | 6.885 | 6.638 |
| 13 | 56.2 | 314.319 | 250.972 |
| 14 | 62.7 | 5.927 | 5.615 |
| 15 | 65.1 | 27.663 | 23.852 |

Example 14

500 g seeds of *Trigonella foenum-graecum* were soaked in 2.5 l water for approximately 24 hours. Following the presoaking the seeds were cooked for 20 minutes and remains of the seeds were removed from the mixture. The extract was chilled.

The aqueous extract was filtered first through a cellulose filter (0.45 μm) and thereafter through a polyamide resin (DPA-6S from Sigma-Aldrich/Supelco) to remove e.g. polyphenolics. This reduces the dry matter content from approx. 14.5 mg/ml to approx 8.5 mg/ml.

The remaining components in the extract were then separated into six fractions using reverse phase chromatography on a size B Lichroprep RP-18 (40-63 μm) (Merck). One ml of enriched plant extract was injected onto the column using the following gradient: 0-1 min $H_2O$/AcN 98:2, and then using a steady gradient from 1-40 min going to 100% AcN. The eluted components were detected using diode array detection (200-600 nm). FIG. 1 shows the chromatogram at 210 nm. Six fraction were collected in the following time intervals (5-10; 10-15; 15-17.5; 17.5-21; 21-24; 24-27 min). Pooled fractions from three repeated injections were taken to dryness using a rotary evaporator and the six fractions were redissolved in 0.5 ml of Milli Q water to give fractions approximately five fold enriched in concentration.

Six HPLC fractions from *Trigonella foenumgraecum* and the basis extract were analysed for antiviral activity towards herpes simplex virus (HSV)-2.

The fractions were mixed with virus ($1 \times 10^5$ plaque-forming units in a 1:1 mixture) and incubated for 15 min at room temperature. The mixtures were added to Vero cell cultures in 10-fold serial dilutions, and virus replication was monitored by cytopathic effect on the cells.

Two days post infection, a 5 fold reduction in virus replication was observed in cultures treated with the basis mixture. No effects of fractions number 3 to 6 were observed. A minor effect appeared in fraction number 2, while fraction number 1 reduced virus replication by 100 about fold.

Based on this experiment, it is concluded that *Trigonella foenumgraecum* has antiviral activity and that this was located in HPLC fraction number 1.

Example 15

Fraction number 1 produced in accordance with example 14 was used for testing the antiviral activity towards HSV-1 (Stain McIntyre) in Vero cells.

The fraction was mixed with virus ($1 \times 10^5$ plaque-forming units in a 1:1 mixture) and incubated for 15 min at room temperature. The mixtures were added to Vero cell cultures, and virus replication was monitored by cytopathic effect on the cells. Blank tests were performed in which either the fraction or the fraction umber 1 was leaved out.

Two days post infection, a growth of Vero cells were observed in vessels containing the mixture of the virus and fraction no. 1. In the blank tests cell death was observed in the vessel that received the virus but not the fraction No. 1, while cell growth was observed in the vessel receiving the fraction No. 1 but not the virus.

Based on this experiment, it is concluded that the content of fraction No. 1 has antiviral activity and that the content of fraction No. 1 is not toxic toward the Vero cells.

The invention claimed is:

1. An extract obtained by a process essentially consisting of the following steps:
    (a) preparing a mixture of seeds obtained from *Trigonella foenum-graecum* and aqueous liquid,
    (b) incubating said mixture for at least 3 hours at a temperature between 0 and 45° C.,
    (c) heating of said mixture for a period of time sufficient to release an embryo from the seeds,
    (d) recovering an aqueous liquid extract from mixture, and
    (e) freezing the incubated mixture prior to the heat treatment according to step (c) or freezing the heat-treated mixture.

2. The extract according to claim 1, wherein said step (e) consists essentially of freezing the heat-treated mixture and repeating step (c).

3. An extract fraction obtained by performing reverse phase chromatography on a size B Lichroprep RP-18 (40-63 μm) (Merck) of an extract obtained by a process essentially consisting of the following steps:
    (a) preparing a mixture of seeds obtained from *Trigonella foenum-graecum* and aqueous liquid,
    (b) incubating said mixture for at least 3 hours at a temperature between 0 and 45° C.,
    (c) heating of said mixture for a period of time sufficient to release an embryo from the seeds, and
    (d) recovering an aqueous liquid extract from mixture, wherein the reverse phase chromatography uses the gradient: 0-1 min $H_2O$/AcN 98:2, and then uses a steady gradient from 1-40 min going to 100% AcN and collects the fraction at the time interval between 5 and 10 min.

4. An extract obtained by a process essentially consisting of the following steps:
    (a) preparing a mixture of seeds obtained from *Trigonella foenum-graecum* and aqueous liquid,
    (b) incubating said mixture for at least 3 hours at a temperature between 0 and 45° C.,
    (c) heating of said mixture for a period of time sufficient to release an embryo from the seeds, and
    (d) recovering an aqueous liquid extract from mixture, by a method selected among the group consisting of: membrane filtration, evaporation, precipitation, extraction, azeotrope distillation, lyophilisation, spray drying and combinations thereof.

5. A composition comprising the extract according to claim 1.

6. The composition according to claim 5, wherein the composition is a pharmaceutical composition.

7. The composition according to claim 5, which is a disinfection agent.

* * * * *